(12) United States Patent
Chada et al.

(10) Patent No.: US 10,343,991 B2
(45) Date of Patent: Jul. 9, 2019

(54) C5, C6 SUBSTITUTED AND/OR FUSED OXINDOLES AS ANTI-CANCER AGENTS AND PROCESS FOR PREPARATION THEREOF

(71) Applicant: Council of Scientific & Industrial Research, New Delhi (IN)

(72) Inventors: Raji Reddy Chada, Hyderabad (IN); Srigiridhar Kotamraju, Hyderabad (IN); Santosh Karnewar, Hyderabad (IN); Nagendra Babu Bathini, Hyderabad (IN); Nagarsenkar Atulya, Hyderabad (IN); Anuradha Singampalli, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/802,003

(22) Filed: Nov. 2, 2017

(65) Prior Publication Data
US 2018/0127365 A1    May 10, 2018

(30) Foreign Application Priority Data

Nov. 2, 2016 (IN) .............................. 201611037409

(51) Int. Cl.
| | | |
|---|---|---|
| C07D 209/34 | (2006.01) | |
| C07D 491/048 | (2006.01) | |
| C07D 403/14 | (2006.01) | |
| C07D 409/06 | (2006.01) | |
| C07D 403/06 | (2006.01) | |
| C07D 405/06 | (2006.01) | |

(52) U.S. Cl.
CPC ......... *C07D 209/34* (2013.01); *C07D 403/06* (2013.01); *C07D 403/14* (2013.01); *C07D 405/06* (2013.01); *C07D 409/06* (2013.01); *C07D 491/048* (2013.01)

(58) Field of Classification Search
CPC .................................................. C07D 209/34
See application file for complete search history.

(56) References Cited

U.S. PATENT DOCUMENTS

| 4,438,130 A | 3/1984 | Kaplan |
|---|---|---|
| 4,588,591 A | 5/1986 | Kaplan et al. |
| 6,114,300 A | 9/2000 | Bourdin et al. |
| 7,235,563 B2 | 6/2007 | Balog |
| 8,119,652 B2 | 2/2012 | Hamblett et al. |
| 8,133,889 B2 * | 3/2012 | Ortuno ................. C07D 401/12 514/235.2 |

FOREIGN PATENT DOCUMENTS

| WO | WO-93/21185 A1 | 10/1993 |
|---|---|---|
| WO | WO-01/66546 A1 | 9/2001 |
| WO | WO-2008/133273 A1 | 7/2010 |

* cited by examiner

Primary Examiner — Shawquia Jackson
(74) Attorney, Agent, or Firm — Blank Rome LLP

(57) ABSTRACT

The present invention describes the C5,C6 Substituted and/or fused oxindole compounds useful as anti-cancer agents and process for preparation thereof. Particularly the present invention relates to C5,C6 Substituted and/or fused oxindole compounds of formula I.

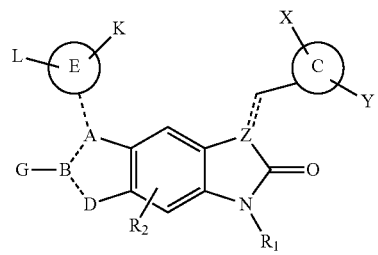

Formula I wherein,
A=C, CH, CH$_2$, None
B=C or CH part of open chain and/or cyclic alkyl/aryl/heteroaryl moiety
G=alkyl, alkenyl, alkynyl, aryl, heteroaryl, heteroalkyl, alkoxy, aryloxy-all these optionally substituted with one or more substituents
D=O, N, S, OH, SH, NH, None
Z=C, CH$_2$
Ring E=aryl/heteroaryl/cycloalkyl optionally substituted with one or more substituents
Ring C=aryl/heteroaryl/cycloalkyl optionally substituted with one or more substituents
L=H, alkyl, alkoxy, halogen, CN, OH, amino, NO$_2$
K=H, alkyl, alkoxy, halogen, CN, OH, amino, NO$_2$
X=H, alkyl, alkoxy, halogen, CN, OH, amino, NO$_2$
Y=H, alkyl, alkoxy, halogen, CN, OH, amino, NO$_2$
R1=H, alkyl
R2=H, alkyl, halogen, CN, NO$_2$, alkoxy, amino, OH

10 Claims, 1 Drawing Sheet

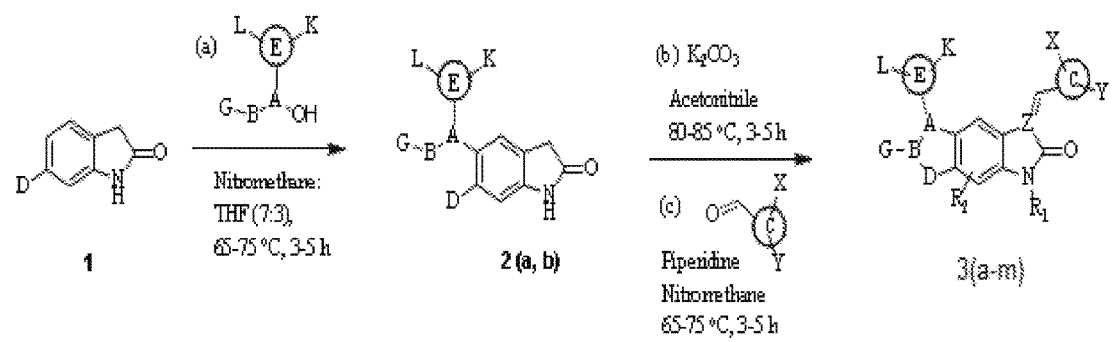

C5, C6 SUBSTITUTED AND/OR FUSED OXINDOLES AS ANTI-CANCER AGENTS AND PROCESS FOR PREPARATION THEREOF

RELATED APPLICATION

This application claims the benefit of Indian Application No. 201611037409, filed Nov. 2, 2016. The entire content of that application is hereby incorporated by reference.

FIELD OF THE INVENTION

The present invention relates to C5, C6 substituted and/or fused oxindole compounds of formula I

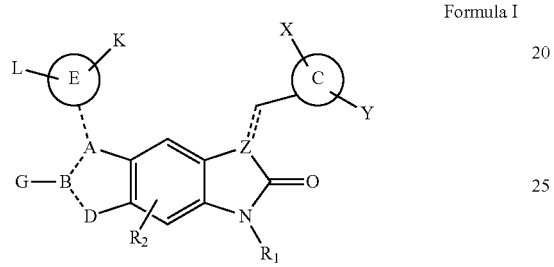

Formula I wherein,
A=C, CH, CH$_2$ or None;
B=C or CH part of open chain and/or cyclic alkyl/aryl/heteroaryl moiety;
G=alkyl, alkenyl, alkynyl, aryl, heteroaryl, heteroalkyl, alkoxy, aryloxy-all these optionally substituted with one or more substituents;
D=O, N, S, OH, SH, NH or None;
Z=C or CH$_2$,
Ring E=aryl/heteroaryl/cycloalkyl optionally substituted with one or more substituents;
Ring C=aryl/heteroaryl/cycloalkyl optionally substituted with one or more substituents;
L=H, alkyl, alkoxy, halogen, CN, OH, amino or NO$_2$,
K=H, alkyl, alkoxy, halogen, CN, OH, amino or NO$_2$,
X=H, alkyl, alkoxy, halogen, CN, OH, amino or NO$_2$,
Y=H, alkyl, alkoxy, halogen, CN, OH, amino or NO$_2$,
R1=H or alkyl;
R2=H, alkyl, halogen, CN, NO$_2$, alkoxy, amino or OH.

Particularly, the present invention relates to a process for the preparation of C5, C6 substituted and/or fused oxindole compounds useful as anticancer agents.

BACKGROUND OF THE INVENTION

3-Alkenyl-oxindole is a prominent structural motif found in a range of medicinally and biologically important compounds, as well as a number of natural products. This core is a part of many chemical compounds that were known to possess wide range of biological activities including anti-inflammatory, antiangiogenic, anticancer, tyrosine kinase A inhibition and cyclooxygenase inhibition. For example sunitinib as anticancer drug, Tenidap for the treatment of arthritis, Ziprasidone for schizophrenia and Ropinirole, a dopamine agonist, for Parkinson's disease are being used.

Among the 3-Alkenyl-oxindoles, compounds with trisubstituted 3-alkenyl unit were found scarcely. The first naturally occurring 3-Alkenyl-oxindoles to be isolated were (E)- and (Z)-3-(3'-methyl-2'-butenylidene)-2-indoline-ones 1. These two yellow pigments were isolated from the rhizomes of *cimicifuga dahurica*, a plant used in Chinese traditional medicine. In 1993, three new oxindole alkaloids neolaugerine 2, isolaugerine 3, and 15-hydroxy-isolaugerine 4, isolated from roots of *Neolaugeria resinosa*.

1.

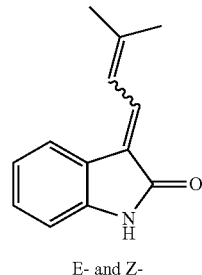

E- and Z-

2.

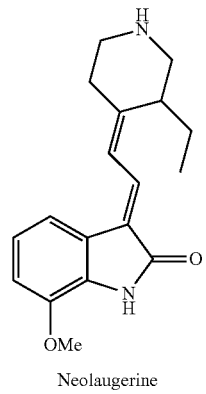

Neolaugerine

3.

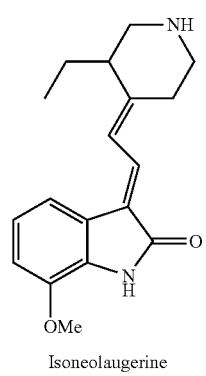

Isoneolaugerine

4.

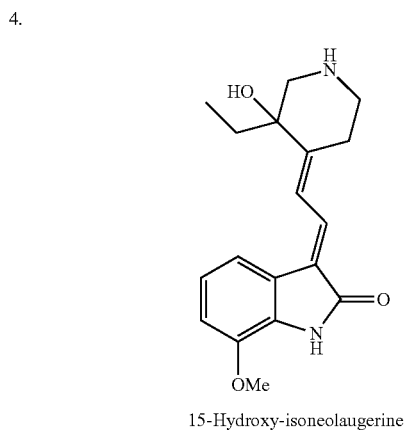

15-Hydroxy-isoneolaugerine

The wide range of biological activities displayed by 3-alkenyl-oxindoles has stimulated considerable pharmaceutical interest. The most successful example is sunitinib 5, which is currently prescribed for the treatment of renal cell sarcoma and gastrointestinal stromal tumours and is undergoing clinical trials studies for the treatment of other solid tumours. A number of related sutent related compound like semaxanib 6, ST280 7, ST458 8 and Tenidap 9 were developed and tested for their effeciencies.

5.

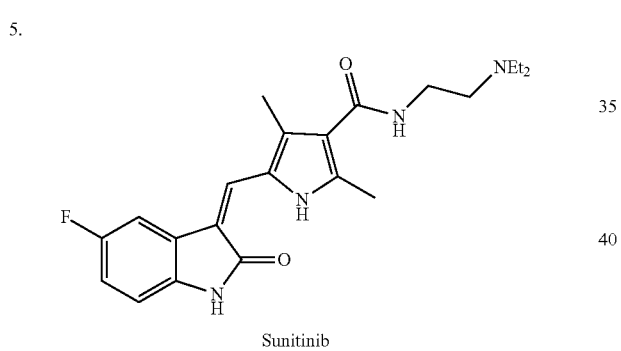

Sunitinib

6.

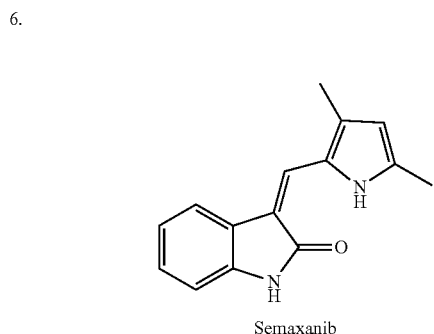

Semaxanib

7.

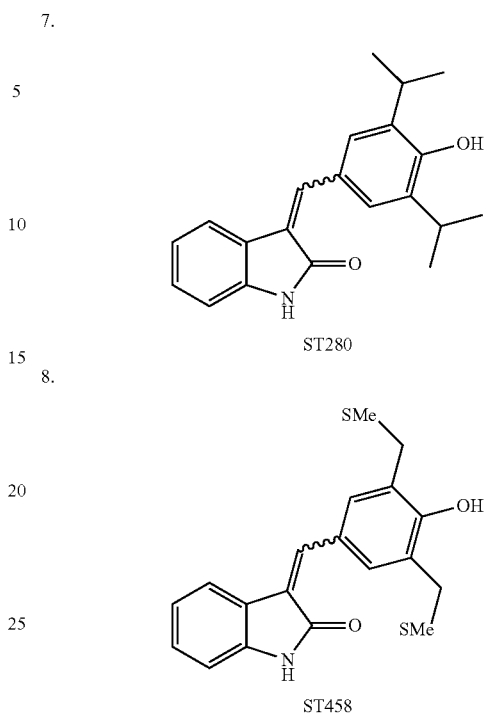

ST280

8.

ST458

9.

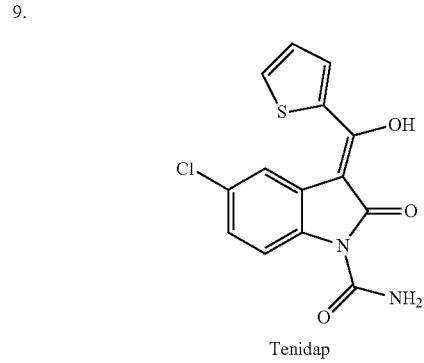

Tenidap

Though a large number of 3-alkenyl oxindoles with diverse structural features were known, there are only few C-5 substituted oxindoles that have been reported till now. The biologically active compounds such as SU9516 10, GW5074 11, NP506 12, CDK2 antagonist 13, JK3 antagonist 14 were found to have C-5 substituted-3-alkenyl oxindole motif.

10.

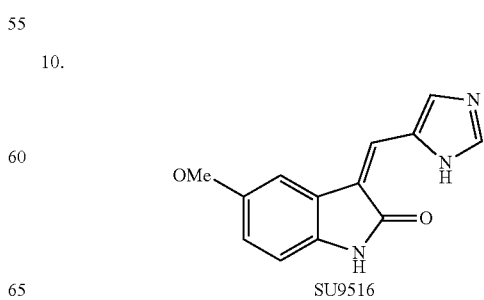

SU9516

-continued

11.

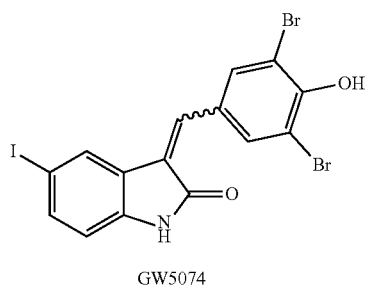

GW5074

12.

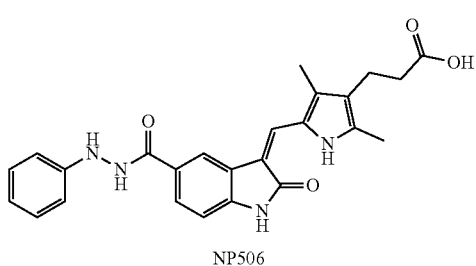

NP506

13.

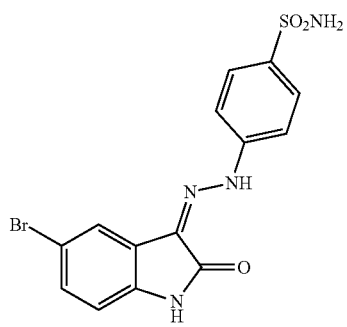

CDK2 antagonist

14.

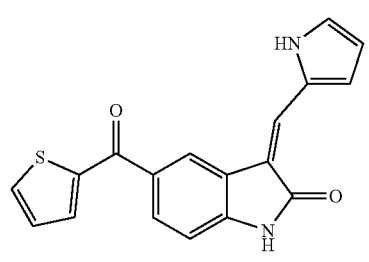

JK3 antagonist

Owing to the importance of 3-alkenyl oxindoles, several research groups have aimed towards identification and development of more potent oxindole derivatives with diverse structural and functional variations at specified positions. Therefore, the synthesis of newly substituted oxindole derivatives that generate new molecular entities is great interest. There are different methods for C-5 substitution of oxindoles such as bromination, nitration, acylation etc., by which the target compounds can be prepared in one or multiple steps. However, the synthetic methods for direct C-5 alkylation of oxindoles are not known or very limited in the literature. In recent years, green and atom-economy synthetic approach is gaining much attention and is practiced to generate eco-friendly protocols. In this direction, use of alcohols as alkylating agents is a simple and viable method since they generate only water as a by-product in the reaction. The availability and the ease of preparation also make them an effective reaction source. Specifically, activated alcohols are more effective and significant due to the stability of corresponding carbonations. The utility of alcohols as alkylating agents in several C—C, C—N and C—O bond formations has been demonstrated under different reaction conditions. 3-alkenyl oxindole compounds that are developed and tested for different biological properties are mentioned in the patents, U.S. Pat. Nos. 4,438,130; 4,588,591; WO1993021185; WO2008133273; U.S. Pat. Nos. 8,119,652; 7,235,563; WO2001066546; U.S. Pat. No. 6,114,300. Based on the present state of art, the design, synthesis and development of 3-alkenyl oxindoles with C-5 substitution employing an eco-friendly protocol and using alcohol as the reaction source is of considerable interest.

OBJECTIVE OF THE INVENTION

The main objective of the present invention is to provide substituted/C5 alkylated and fused oxindole compounds of formula I as anticancer agents.

Another objective of the present invention is to provide a process for the preparation of substituted/C5 alkylated and fused oxindole compounds of formula I.

BRIEF DESCRIPTION OF THE DRAWING

FIG. 1 represents process steps for the preparation of C5, C6 substituted and/or fused oxindoles compounds of formula I.

SUMMARY OF THE INVENTION

Accordingly, present invention provides a compound of formula I

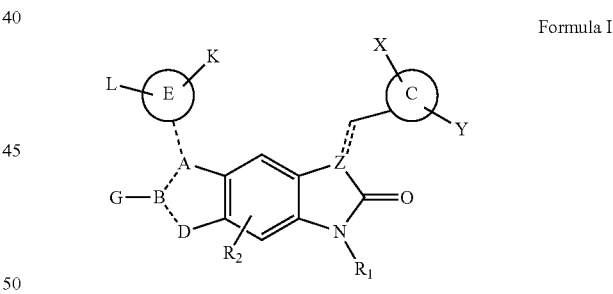

Formula I wherein,
A=C, CH, $CH_2$ or none;
B=C or CH part of open chain and/or cyclic alkyl/aryl/heteroaryl moiety;
G=alkyl, alkenyl, alkynyl, aryl, heteroaryl, heteroalkyl, alkoxy, aryloxy-all these optionally substituted with one or more substituents;
D=O, N, S, OH, SH, NH or None;
Z=C or $CH_2$,
Ring E=aryl/heteroaryl/cycloalkyl optionally substituted with one or more substituents;
Ring C=aryl/heteroaryl/cycloalkyl optionally substituted with one or more substituents;
L=H, alkyl, alkoxy, halogen, CN, OH, amino or $NO_2$;
K=H, alkyl, alkoxy, halogen, CN, OH, amino or $NO_2$;
X=H, alkyl, alkoxy, halogen, CN, OH, amino or $NO_2$;

Y=H, alkyl, alkoxy, halogen, CN, OH, amino or $NO_2$,
R1=H or alkyl;
R2=H, alkyl, halogen, CN, $NO_2$, alkoxy, amino or OH.

In an embodiment of the present invention, representative compounds of formula I comprising:
  i. 5-(1,3-Diphenylprop-2-yn-1-yl)-6-hydroxyindolin-2-one (2a);
  ii. 5-(4-(Benzyloxy)-1-(2, 3-dimethoxyphenyl) but-2-ynyl)-6-hydroxyindolin-2-one (2b);
  iii. 2-Benzyl-3-phenyl-5H-furo[3,2-f]indol-6(7H)-one (3a);
  iv. 2-(2-(Benzyloxy) ethyl)-3-(2, 3-dimethoxyphenyl)-5H-furo [3, 2-f] indol-6(7H)-one (3b);
  v. (Z)-3-((3,5-dimethyl-1H-pyrrol-2-yl)methylene)-5-(1,3-diphenylprop-2-yn-1-yl)-6-hydroxyindolin-2-one (3c);
  vi. (Z)-5-(1,3-diphenylprop-2-yn-1-yl)-6-hydroxy-3-((3-methylthiophen-2-yl)methylene)indolin-2-one (3d);
  vii. (Z)-3-((4-(dimethylamino)naphthalen-1-yl)methylene)-5-(1,3-diphenylprop-2-yn-1-yl)-6-hydroxyindolin-2-one (3e);
  viii. (Z)-5-(3-(benzyloxy)-1-(2,3-dimethoxyphenyl)prop-2-yn-1-yl)-3-((3,5-dimethyl-1H-pyrrol-2-yl)methylene)-6-hydroxyindolin-2-one (3f);
  ix. (Z)-3-((3,5-dimethyl-1H-pyrrol-2-yl)methylene)-6-hydroxy-5-(3-phenyl-1-(1-tosyl-1H-indol-3-yl)prop-2-yn-1-yl)indolin-2-one (3g);
  x. (Z)-2-benzyl-5-((3,5-dimethyl-1H-pyrrol-2-yl)methylene)-3-phenyl-5H-furo[3,2-f]indol-6(7H)-one (3h);
  xi. (Z)-2-benzyl-5-((3-methylthiophen-2-yl)methylene)-3-phenyl-5H-furo[3,2-f]indol-6(7H)-one (3i);
  xii. (Z)-2-benzyl-5-((4-(dimethylamino)naphthalen-1-yl)methylene)-3-phenyl-5H-furo[3,2-f]indol-6(7H)-one (3j);
  xiii. (Z)-2-((benzyloxy)methyl)-3-(2,3-dimethoxyphenyl)-5-((3,5-dimethyl-1H-pyrrol-2-yl)methylene)-5H-furo[3,2-f]indol-6(7H)-one (3k);
  xiv. (Z)-2-((benzyloxy)methyl)-3-(2,3-dimethoxyphenyl)-5-((3-methylthiophen-2-yl)methylene)-5H-furo[3,2-f]indol-6(7H)-one (3l);
  xv. (Z)-2-benzyl-5-((3,5-dimethyl-1H-pyrrol-2-yl)methylene)-3-(1-tosyl-1H-indol-3-yl)-5H-furo[3,2-f]indol-6(7H)-one (3m).

In yet another embodiment, present invention provides a process for the preparation of compound of formula I and the said process comprising the steps of:
  a) alkylating oxindole compound of formula 1 with compound of formula (a) at a temperature in the range of 65 to 75° C. for a period in the range of 3 to 5 h followed by purifying to obtain compound of formula 2;

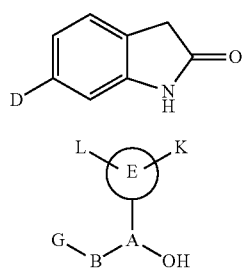

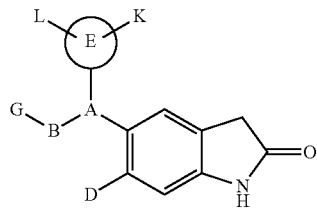

b) cyclizating the compound of formula 2 as obtained in step (a) using base at a temperature in the range of 70 to 80° C. for a period in the range of 3-5 h followed by purifying to obtain compound of formula 3a and 3b;
  c) condensating the compound of formula 2 as obtained in step (a) with aldehyde of formula (c) at active methylene at a temperature in the range of 70 to 80° C. for a period in the range of 3-5 h, purifying to obtain compound of formula 3c-3g;
  d) cyclizating the compound of formula 2 as obtained in step (a) using base at a temperature in the range of 70 to 80° C. for a period in the range of 3-5 h followed by condensating with aldehyde of formula (c) at active methylene at a temperature in the range of 70 to 80° C. for a period in the range of 3-5 h, purifying to obtain compound of formula 3h-3m.

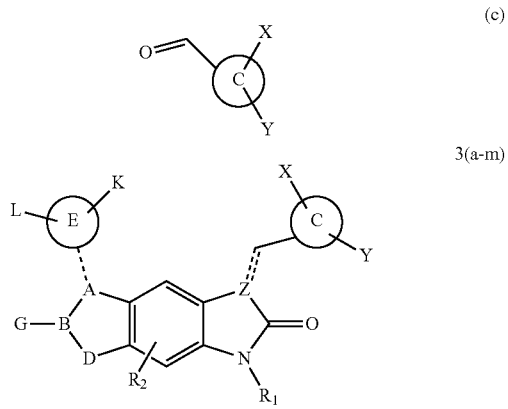

In yet another embodiment of the present invention, purification of the products is carried out by crystallization or column chromatography. In yet another embodiment of the present invention, alkylation is performed using acid catalyst, nitromethane and THF (tetrahydrofuran).

In yet another embodiment of the present invention, the base used is selected from the group consisting of $K_2CO_3$, NaOH, KOH, $Na_2CO_3$ or $NaHCO_3$ In yet another embodiment of the present invention, condensation reaction with aldehyde is carried out in alcoholic solvent and organic base.

In yet another embodiment of the present invention, the alcoholic solvent used is selected from the group consisting of methanol, ethanol, propanol or butanol.

In yet another embodiment of the present invention, the organic base used is selected from the group consisting of piperidine, pyrrolidine or trimethylamine.

In yet another embodiment of the present invention, compound of formula I are useful as anti-cancer agents.

In yet another embodiment of the present invention, percentage of cell viability against different cancer cell lines ranging between 20 to 160% at 10 μM.

DETAILED DESCRIPTION OF THE INVENTION

Present invention provides a C5, C6 substituted and/or fused oxindoles compounds of formula I exhibit anti-cancer properties.

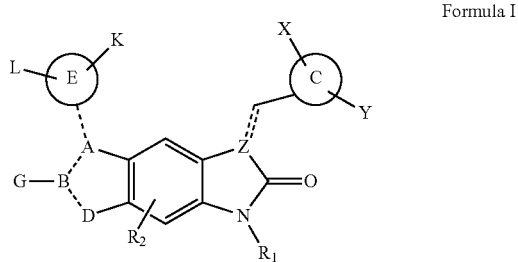

Formula I wherein,

A=C, CH, CH$_2$ or None;
B=C or CH part of open chain and/or cyclic alkyl/aryl/heteroaryl moiety;
G=alkyl, alkenyl, alkynyl, aryl, heteroaryl, heteroalkyl, alkoxy, aryloxy-all these optionally substituted with one or more substituents;
D=O, N, S, OH, SH, NH or None;
Z=C or CH$_2$,
Ring E=aryl/heteroaryl/cycloalkyl optionally substituted with one or more substituents;
Ring C=aryl/heteroaryl/cycloalkyl optionally substituted with one or more substituents;
L=H, alkyl, alkoxy, halogen, CN, OH, amino or NO$_2$;
K=H, alkyl, alkoxy, halogen, CN, OH, amino or NO$_2$;
X=H, alkyl, alkoxy, halogen, CN, OH, amino or NO$_2$;
Y=H, alkyl, alkoxy, halogen, CN, OH, amino or NO$_2$;
R1=H or alkyl;
R2=H, alkyl, halogen, CN, NO$_2$, alkoxy, amino or OH.

The synthesis of these compounds has been carried out as described in FIG. 1. A large number of various C5,C6 substituted and/or fused oxindoles compounds possessing diversely functionalized architecture were found to exhibit several biological properties. These functionalities are prominent structural motifs of new medicines from different pharmacological groups. The development of new structural scaffolds of substituted and/or fused oxindole architecture is very important for the drug discovery process. In this connection a variety of substituted and/or fused oxindole derivatives were developed as depicted in the above formula I.

The process for the synthesis of these new substituted and/or fused oxindole compounds starts from simple oxindole compound and involves operationally simple and highly efficient synthetic protocol giving rise to the desired products substituted and/or fused oxindoles in high yields.

The process for preparation of the C5,C6 substituted and/or fused oxindole compounds comprising the steps of:
(a) alkylation on oxindole;
(b) Optionally base mediated cyclization;
(c) Optionally condensation with aldehyde at active methylene;
(d) purification.

The first step is the alkylation on indole is performed using acid catalyst, nitromethane and THF at 65-75° C. for 3-5 h.

The second step is base mediated cyclization is carried out using any of the bases selected from K$_2$CO$_3$, NaOH, KOH, Na$_2$CO$_3$, NaHCO$_3$ in acetonitrile at 70-80° C. for 3-5 h.

The third step is condensation reaction with aldehyde at active methylene of oxindole is carried out in alcoholic solvent selected from methanol, ethanol, propanol, butanol and an organic base selected from piperidine, pyrrolidine, trimethylamine at 70-80° C. for 3-5 h.

The purification of the products is carried out by crystallization or column chromatography.

EXAMPLES

Following examples are given by way of illustration and therefore should not be construed to limit the scope of the invention.

Procedure 1

Preparation of Compound 2a and 2b

6-Hydoxy oxindole (10 mmol, 1 equiv) was dissolved in nitro methane and THF (7:3). Propargyl alcohol (10 mmol, 1 equiv) was then added, followed up by 0.2 equiv of pTSA. Mixture was stirred at room temperature (25° C.) for 6 h. Later it was extracted with ethyl acetate and product was purified using column chromatography (ethyl acetate and hexanes as eluent).

Procedure 2

Preparation of Compound 3a and 3b

C-5 Propargylated-6-hydroxy oxindole 2 (1 equiv) was refluxed with K$_2$CO$_3$ (0.2 equiv) in acetonitrile for 6 h. After completion of the reaction, mixture was cooled to room temperature, extracted with ethyl acetate. The combined organic layers were concentrated and the obtained crude product was purified using column chromatography (ethyl acetate and hexanes as eluent).

Procedure 3

Preparation of Compound 3c, 3d, 3e, 3f and 3g

C-5 Propargylated-6-hydroxy oxindole 2 (1 equiv) was refluxed with aldehyde (1.1 equiv) in ethanol using piperidine (0.1 equiv) as base to give the product. The product was filtered and washed 3 times using cooled ethanol to obtain the pure product.

Procedure 4

Preparation of Compound 3h, 3i, 3j, 3k, 3l and 3m

Procedure II followed by procedure III will give the required products.

TABLE 1
| Reactant 1 | Reactant 2 | Reagents/ Solvent | Reaction termperature/ time | Product |
|---|---|---|---|---|
| 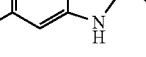 |  | PTSA/ CH₃NO₂ + THF | rt/6 h | 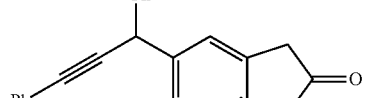 2a |
| 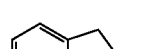 | 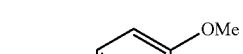 | PTSA/ CH₃NO₂ + THF | rt/5 h | 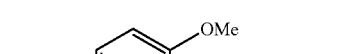 2b |
|  | — | K₂CO₃/ CH₃CN | 80° C./6 h | 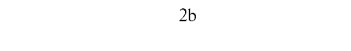 3a |
| 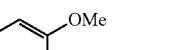 | — | K₂CO₃/ CH₃CN | 80° C./7 h | 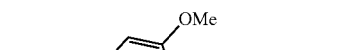 3b |
|  | 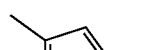 | Piperidine/ Ethanol | 80° C./2 h |  3c |
| 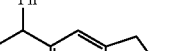 | 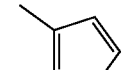 | Piperidine/ Ethanol | 80° C./2 h |  3d |

TABLE 1-continued
| Reactant 1 | Reactant 2 | Reagents/ Solvent | Reaction termperature/ time | Product |
|---|---|---|---|---|
| 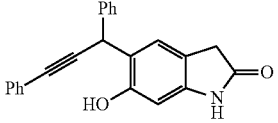 [SMILES: O=C1Cc2cc(C(C#Cc3ccccc3)c3ccccc3)c(O)cc2N1] | 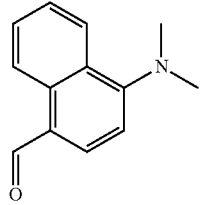 | Piperidine/ Ethanol | 80° C./3 h | 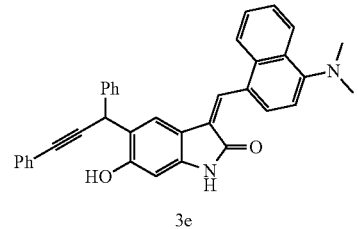 [SMILES: CN(C)c1ccc(/C=C2\C(=O)Nc3cc(O)c(C(C#Cc4ccccc4)c4ccccc4)cc32)c2ccccc12]<br>3e |
| 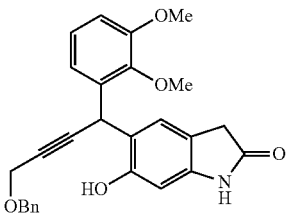 [SMILES: COc1cccc(C(C#CCOCc2ccccc2)c2cc3c(cc2O)NC(=O)C3)c1OC] | 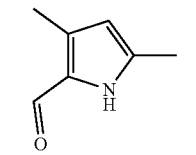 | Piperidine/ Ethanol | 80° C./2 h | 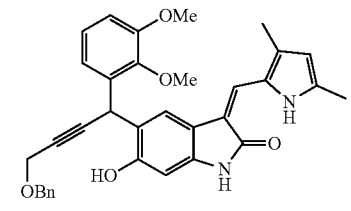<br>3f |
| 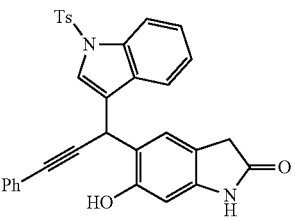 [SMILES: Cc1ccc(S(=O)(=O)n2cc(C(C#Cc3ccccc3)c3cc4c(cc3O)NC(=O)C4)c3ccccc32)cc1] | 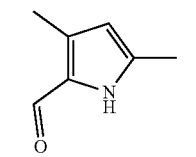 | Piperidine/ Ethanol | 80° C./2 h | 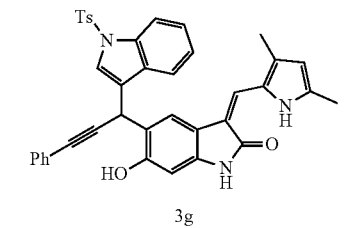 [SMILES: Cc1ccc(S(=O)(=O)n2cc(C(C#Cc3ccccc3)c3cc4c(cc3O)NC(=O)/C4=C\c3[nH]c(C)cc3C)c3ccccc32)cc1]<br>3g |
| 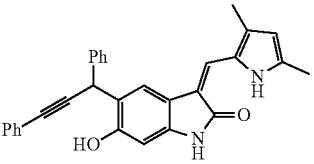 [SMILES: Cc1cc(C)c(/C=C2\C(=O)Nc3cc(O)c(C(C#Cc4ccccc4)c4ccccc4)cc32)[nH]1] | — | $K_2CO_3$/ $CH_3CN$ | 80° C./8 h | 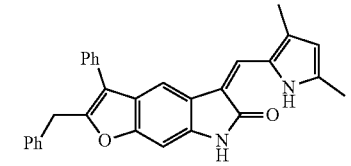<br>3h |
| 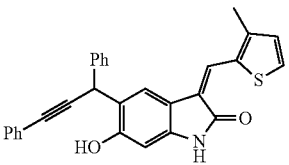 [SMILES: Cc1ccsc1/C=C1\C(=O)Nc2cc(O)c(C(C#Cc3ccccc3)c3ccccc3)cc21] | — | $K_2CO_3$/ $CH_3CN$ | 80° C./6 h | 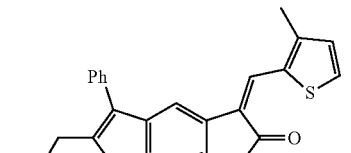<br>3i |
| 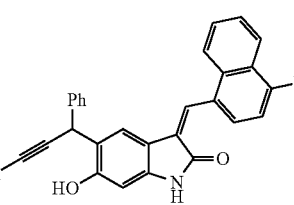 | — | $K_2CO_3$/ $CH_3CN$ | 80° C./7 h | 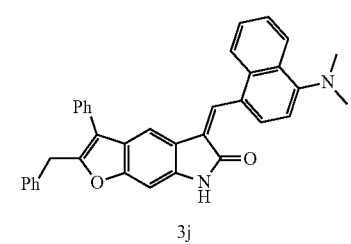 [SMILES: CN(C)c1ccc(/C=C2\C(=O)Nc3cc4oc(Cc5ccccc5)c(-c5ccccc5)c4cc32)c2ccccc12]<br>3j |

TABLE 1-continued

| Reactant 1 | Reactant 2 | Reagents/Solvent | Reaction temperature/time | Product |
|---|---|---|---|---|
| (structure) | — | K₂CO₃/CH₃CN | 80° C./8 h | 3k |
| (structure) | — | K₂CO₃/CH₃CN | 80° C./6 h | 3l |
| (structure) | — | K₂CO₃/CH₃CN | 80° C./7 h | 3m |

Example 1

5-(1,3-Diphenylprop-2-yn-1-yl)-6-hydroxyindolin-2-one (2a)

Appearance—Pale yellow. M.P: 195-196° C. $^1$H NMR (300 MHz DMSO-$d_6$): δ 9.96 (s, 1H), 9.21 (s, 1H), 7.42 (s, 4H), 7.3-7.1 (m, 7H), 6.4 (s, 1H), 5.57 (s, 1H), 3.29 (s, 2H). $^{13}$C NMR (75 MHz, DMSO-$d_6$): δ 176.9, 153.2, 143.2, 142.0, 131.3, 128.5, 128.2, 128.1, 127.2, 126.3, 124.0, 122.7, 120.3, 116.0, 97.2, 91.4, 82.8, 35.4, 35.2. HRMS m/z: (ESI): Calculated for 340.1332 [M+H]$^+$, found: 340.1331 [M+H]$^+$. IR (KBr): 3226, 2924, 1633, 1334, 1206 cm$^{-1}$.

Example 2

5-(4-(Benzyloxy)-1-(2, 3-dimethoxyphenyl) but-2-ynyl)-6-hydroxyindolin-2-one (2b)

Appearance—brown solid. M.P: 177-179° C. $^1$H NMR (300 MHz DMSO-$d_6$): δ 910.25 (s, 1H), 9.81 (s, 1H), 7.38-6.75 (m, 9H), 6.38 (s, 1H), 5.58 (s, 1H), 4.42 (s, 2H), 3.81 (s, 2H), 3.60 (s, 2H), 3.31 (s, 2H). $^{13}$C NMR (75 MHz, DMSO-$d_6$): δ 176.4, 153.0, 152.8, 150.4, 148.7, 146.7, 142.1, 140.6, 138.2, 128.1, 127.3, 125.5, 124.1, 122.5, 121.2, 114.1, 112.4, 92.6, 71.6, 67.6, 67.2, 60.1, 59.9, 55.6, 35.3, 27.5. ESI-MS: m/z 466.3 [M+Na]$^+$. IR (KBr): 3374, 2933, 2844, 1678, 1630, 1477, 1327, 1273, 1210, 1055, 746, 645 cm$^{-1}$.

Example 3

2-Benzyl-3-phenyl-5H-furo[3,2-f]indol-6(7H)-one (3a)

Appearance—Red solid. M.P: 196-198° C. $^1$H NMR (300 MHz DMSO-$d_6$): δ 10.29 (s, 1H), 7.50-7.13 (m, 12H), 6.92 (s, 1H), 4.13 (s, 2H), 3.41 (s, 2H). $^{13}$C NMR (75 MHz, DMSO-$d_6$): δ 175.9, 153.2, 149.9, 140.7, 137.4, 131.8, 128.2, 128.0, 127.7, 126.7, 125.9, 121.8, 120.5, 114.8, 95.4, 92.9, 35.2, 32.1. HRMS m/z: (ESI): C$_{23}$H$_{17}$NO$_2$: 340.1332 [M+H]$^+$, found: 340.1349 [M+H]$^+$. IR (KBr): 3630, 3182, 2924, 1696, 1465, 766 cm$^{-1}$.

Example 4

2-(2-(Benzyloxy) ethyl)-3-(2, 3-dimethoxyphenyl)-5H-furo [3, 2-f] indol-6(7H)-one (3b)

Appearance—White solid. M.P: 120-122° C. $^1$H NMR (300 MHz DMSO-$d_6$): δ 10.38 (s, 1H), 7.3-.6.85 (m, 10H), 4.4 (s, 2H), 3.85 (s, 3H), 3.71 (t, J=6.9, 5.9 Hz, 2H), 3.45 (s, 2H), 3.35 (s, 3H), 2.95 (t, J=6.9, 5.9 Hz, 2H). $^{13}$C NMR (75 MHz, DMSO-$d_6$): δ 176, 152.4, 150, 146.3, 141.6, 140.2, 137.7, 127.7, 126.8, 125.1, 124.3, 123.7, 122.1, 121.5, 120.8, 115.9, 115.3, 113.7, 112.0, 92.1, 71.2, 66.7, 59.7, 59.8, 55.2, 34.9, 27.1. ESI-MS: m/z 466 [M+Na]$^+$. IR (KBr): 3420, 2926, 2857, 1703, 1630, 1464, 1082, 837, 743 cm$^{-1}$.

Example 5

(Z)-3-((3,5-dimethyl-1H-pyrrol-2-yl)methylene)-5-(1,3-diphenylprop-2-yn-1-yl)-6-hydroxyindolin-2-one (3c)

Appearance—Brown. M.P:173-179° C. $^1$H NMR (300 MHz DMSO-$d_6$): δ 10.23 (s, 1H), 9.91 (s, 1H), 7.53-7.02 (m, 12H), 6.89 (s, 1H), 6.43 (s, 1H), 5.48 (s, 1H), 2.53 (m, 3H), 2.37 (s, 3H). $^{13}$C NMR (75 MHz, DMSO-$d_6$): δ 169.8, 155.6, 143.0, 142.7, 141.8, 131.2, 130.9, 128.4, 128.3, 128.1, 127.3, 126.4, 124.2, 123.2, 122.8, 120.9, 120.5, 112.2, 97.4, 95.3, 91.4, 83.4, 29.7, 14.3, 13.9. HRMS m/z: (ESI): Calculated for $C_{30}H_{24}N_2O_2$: 445.1911 [M+H]$^+$, found: 445.1876 [M+H]$^+$. IR (KBr): 2923, 1659, 1596, 1322, 1275, 1171, 751 cm$^{-1}$.

Example 6

(Z)-5-(1,3-diphenylprop-2-yn-1-yl)-6-hydroxy-3-((3-methylthiophen-2-yl)methylene)indolin-2-one (3d)

Appearance—Brown. M.P: 182-185° C. $^1$H NMR (300 MHz DMSO-$d_6$): δ 10.4 (s, 1H), 10.22 (s, 1H), 6.65-6.17 (m, 13H), 6.99 (s, 1H), 6.42 (s, 1H), 5.48 (s, 1H), 2.34 (s, 3H). $^{13}$C NMR (75 MHz, DMSO-$d_6$): δ 169.8, 155.6, 143.0, 142.7, 141.8, 131.2, 130.8, 129.9, 128.4, 128.2, 128.1, 127.3, 126.3, 124.2, 123.2, 122.8, 120.9, 120.5, 112.2, 97.4, 95.3, 91.4, 83.4, 28.9, 13.8. HRMS m/z: (ESI): Calculated for $C_{29}H_{21}NO_2S$: 448.1366 [M+H]$^+$, found: 448.1335 [M+H]$^+$. IR (KBr): 3214, 1922, 1689, 1630, 1597, 1323, 1168, 696 cm$^{-1}$.

Example 7

(Z)-3-((4-(dimethylamino)naphthalen-1-yl)methylene)-5-(1,3-diphenylprop-2-yn-1-yl)-6-hydroxyindolin-2-one (3e)

Appearance—Orange solid. M.P:188-192° C. $^1$H NMR (300 MHz, DMSO-$d_6$): δ 10.74 (s, 1H), 8.30-8.22 (s, 1H), 7.96 (s, 1H), 7.90-7.86 (m, 2H), 7.64-7.50 (m, 3H), 7.34-6.97 (m, 13H), 4.13 (s, 2H), 2.88 (s, 6H). 13CNMR (125 MHz, DMSO-$d_6$): δ 168.6, 154.3, 152.0, 140.5, 137.3, 131.7, 131.5, 131.0, 128.7, 128.4, 128.2, 127.9, 127.5, 127.4, 126.7, 126.4, 126.1, 125.2, 125.0, 124.8, 124.7, 121.2, 117.7, 117.3, 114.1, 112.4, 93.1, 44.4, 31.9. HRMS m/z: (ESI): Calculated for $C_{36}H_{29}O_2N_2$ [M+H]$^+$ 521.2223, found 521.2209 [M+H]$^+$. IR (KBr): 3411, 3100, 2924, 1676, 1340, 1109, 699 cm$^{-1}$.

Example 8

(Z)-5-(3-(benzyloxy)-1-(2,3-dimethoxyphenyl)prop-2-yn-1-yl)-3-((3,5-dimethyl-1H-pyrrol-2-yl)methylene)-6-hydroxyindolin-2-one (3f)

Appearance—brown solid M.P: 181-183° C. $^1$H NMR (300 MHz, DMSO-$d_6$): δ 13.6 (s, 1H), 11.1 (s, 1H), 10.0 (s, 1H), 8.1 (s, 1H), 7.8-7.7 (m, 7H), 7.4-7.2 (m, 3H), 6.8 (s, 1H), 6.3 (s, 1H), 6.1 (s, 1H), 5.0 (s, 2H), 4.6 (s, 2H), 4.2 (s, 3H), 4.1 (s, 3H), 2.8 (s, 5H), 2.6 (s, 3H). $^{13}$C NMR (125 MHz, DMSO-$d_6$): δ 169.8, 153.2, 152.2, 145.7, 138.2, 137.5, 135.3, 133.9, 129.4, 128.1, 127.8, 127.5, 127.2, 126.1, 123.5, 120.2, 120.1, 119.8, 118.3, 116.6, 113.5, 111.8, 111.2, 97.1, 78.7, 70.5, 59.7, 57.3, 55.5, 29.5, 13.3, 11.1. HRMS m/z: Calculated for $C_{34}H_{33}O_5N_2$ [M+H]$^+$ 549.2384, found 549.2376 [M+H]$^+$. IR (KBr): 3382, 2925, 2853, 1660, 1629, 1274, 1149, 1063, 969, 806, 766, 743 cm$^{-1}$.

Example 9

(Z)-3-((3,5-dimethyl-1H-pyrrol-2-yl)methylene)-6-hydroxy-5-(3-phenyl-1-(1-tosyl-1H-indol-3-yl)prop-2-yn-1-yl)indolin-2-one (3g)

Appearance—brown solid M.P: 185-186° C. $^1$H NMR (300 MHz, DMSO-$d_6$): δ 13.15 (s, 1H), 10.64 (s, 1H), 9.99 (s, 1H), 7.97-7.14 (m, 17H), 6.47 (s, 1H), 5.75 (s, 1H), 2.29 (d, J=3.0 Hz, 6H), 2.20 (s, 3H). $^{13}$C NMR (125 MHz, DMSO-$d_6$): δ 169.9, 152.9, 145.2, 144.1, 138.5, 134.6, 134.2, 134.0, 131.4, 130.0, 129.8, 129.0, 128.1, 128.6, 128.3, 126.7, 126.3, 124.8, 123.9, 123.7, 123.3, 122.7, 121.1, 120.0, 118.7, 117.6, 113.3, 111.9, 97.1, 90.4, 81.9, 29.7, 23.0, 13.9, 10.9. ESI-MS: m/z 638 [M+H]$^+$. IR (KBr): 2923, 1631, 1219, 772 cm$^{-1}$.

Example 10

(Z)-2-benzyl-5-((3,5-dimethyl-1H-pyrrol-2-yl)methylene)-3-phenyl-5H-furo[3,2-f]indol-6(7H)-one (3h)

Appearance—Yellow. M.P: 186-188° C. $^1$H NMR (300 MHz DMSO-$d_6$): δ 10.86 (s, 1H), 7.87 (s, 1H), 7.63-7.17 (m, 11H), 7.01 (s, 1H), 5.96 (s, 1H), 4.15 (s, 2H), 2.27 (d, J=6.7 Hz, 6H). $^{13}$C NMR (75 MHz, DMSO-$d_6$): δ 169.9, 150.6, 149.2, 148.1, 142.9, 137.8, 131.6, 129.0, 128.9, 128.8, 128.6, 128.5, 128.2, 128.1, 127.4, 126.5, 121.8, 115.3, 113.5, 112.6, 92.9, 94.1, 30.6, 13.4, 11.4. HRMS m/z: (ESI): Calculated for $C_{30}H_{24}N_2O_2$: 445.1911 [M+H]$^+$, found: 445.1937 [M+H]$^+$. IR (KBr): 2919, 1693, 1665, 1558, 1457, 1331, 1145, 768 cm$^{-1}$.

Example 11

(Z)-2-benzyl-5-((3-methylthiophen-2-yl)methylene)-3-phenyl-5H-furo[3,2-f]indol-6(7H)-one (3i)

Appearance—Yellow. M.P: 165-168° C. $^1$H NMR (300 MHz DMSO-$d_6$): δ 10.40 (s, 1H), 8.37 (s, 1H), 7.83-7.13 (m, 15H), 7.01-6.92 (m, 2H), 4.19 (d, J=10.1 Hz, 2H), 2.44 (s, 3H). $^{13}$C NMR (75 MHz, DMSO-$d_6$): δ 169.2, 154.3, 150.4, 140.4, 137.3, 131.4, 131.7, 130.2, 128.4, 128.1, 128.3, 128.4, 127.7, 127.8, 126.8, 125.9, 123.5, 121.6, 117.7, 117.4, 114.4, 95.4, 93.2, 32.1, 14.4. HRMS m/z: (ESI): Calculated for $C_{29}H_{21}NO_2S$: 448.1366 [M+H]$^+$, found: 448.1331 [M+H]$^+$. IR (KBr): 3170, 2920, 1694, 1601, 1457, 1145, 701 cm$^{-1}$.

Example 12

(Z)-2-benzyl-5-((4-(dimethylamino)naphthalen-1-yl)methylene)-3-phenyl-5H-furo[3,2-f]indol-6(7H)-one (3j)

Appearance: Orange solid M.P: 241-245° C. $^1$H NMR (300 MHz, DMSO-$d_6$): δ 10.73 (s, 1H), 7.97 (s, 1H), 7.90-7.81 (m, 2H), 7.66-7.50 (m, 2H), 7.47-7.05 (m, 12H), 6.99 (s, 1H), 4.13 (s, 2H), 2.87 (s, 6H). $^{13}$C NMR (75 MHz, DMSO-$d_6$): δ 168.7, 154.3, 152.2, 151.0, 140.6, 137.5, 132.1, 131.5, 131.0, 128.8, 128.5, 128.0, 127.9, 127.5, 127.1, 126.7, 126.4, 125.4, 125.2, 125.0, 124.9, 121.3, 117.9, 117.4, 114.2, 112.7, 93.3, 44.5, 31.9. HRMS m/z:

(ESI): Calculated for $C_{36}H_{29}O_2N_2$ [M+H]$^+$ 521.2223, found 521.2210 [M+H]$^+$. IR (KBr): 3446, 3139, 2836, 1695, 1328, 1145, 770 cm$^{-1}$.

Example 13

(Z)-2-((benzyloxy)methyl)-3-(2,3-dimethoxyphenyl)-5-((3,5-dimethyl-1H-pyrrol-2-yl)methylene)-5H-furo[3,2-f]indol-6(7H)-one (3k)

Appearance—red solid M.P: 208-212° C. $^1$H NMR (300 MHz, DMSO-d$_6$): δ 10.65 (s, 1H), 7.39-6.91 (m, 12H), 5.85 (s, 1H), 4.39 (s, 2H), 3.86 (s, 6H), 3.74 (t, J=6.60, 6.42 Hz, 2H), 2.96 (t, J=6.6, 6.4 Hz, 2H), 2.28 (s, 3H), 2.22 (s, 3H). $^{13}$C NMR (125 MHz, DMSO-d$_6$): δ 169.7, 152.7, 152.5, 150.4, 146.8, 137.9, 135.8, 134.4, 130.3, 127.8, 127.1, 126.2, 125.8, 123.9, 122.9, 122.8, 122.1, 121.7, 114.1, 118.3, 112.8, 111.8, 108.4, 92.4, 71.8, 67.2, 59.9, 55.4, 13.3, 11.3. HRMS m/z: (ESI): Calculated for $C_{34}H_{33}O_5N_2$ [M+H]$^+$ 549.2384, found 549.2376 [M+H]$^+$. IR (KBr): 3175, 2926, 1692, 1463, 1262, 834, 699 cm$^{-1}$.

Example 14

(Z)-2-((benzyloxy)methyl)-3-(2,3-dimethoxyphenyl)-5-((3-methylthiophen-2-yl)methylene)-5H-furo[3,2-f]indol-6(7H)-one (3l)

Appearance—Yellow solid M.P:194-196° C. $^1$H NMR (300 MHz, DMSO-d$_6$): δ 10.59 (s, 1H), 8.10 (s, 1H), 7.63 (m, 2H), 7.34-6.91 (m, 11H), 4.42 (s, 2H), 3.87 (s, 4H), 3.73 (t, J=6.6, 6.4 Hz, 2H), 2.98 (t, J=6.6, 6.4 Hz, 2H), 2.35 (s, 3H). $^{13}$CNMR (75 MHz, DMSO-d$_6$): δ 169.4, 154.1, 152.7, 151.0, 146.7, 143.1, 140.0, 138.0, 130.7, 130.6, 127.9, 127.8, 127.1, 127.1, 127.0, 125.1, 123.8, 123.7, 123.5, 122.6, 117.1, 115.0, 114.1, 112.6, 93.2, 71.7, 67.0, 59.9, 55.7, 27.6, 14.4. HRMS m/z: (ESI): Calculated for $C_{33}H_{30}O_5NS$ [M+H]$^+$ 552.1839, found 552.1827 [M+H]$^+$. IR (KBr): 3213, 2921, 2851, 1687, 1462, 1264, 1140, 743, 697 cm$^{-1}$.

Example 15

(Z)-2-benzyl-5-((3,5-dimethyl-1H-pyrrol-2-yl)methylene)-3-(1-tosyl-1H-indol-3-yl)-5H-furo[3,2-f]indol-6(7H)-one (3m)

Appearance—Yellow solid M.P:174-176° C. $^1$H NMR (300 MHz, DMSO-d$_6$): δ 10.53 (s, 1H), 8.06 (d, J=3.0 Hz, 1H), 7.86 (d, J=3.0 Hz, 2H), 7.65 (s, 1H), 7.46-7.09 (m, 13H), 6.99 (s, 1H), 5.85 (s, 1H), 4.01 (s, 2H), 2.36 (s, 6H), 2.24 (s, 3H). $^{13}$CNMR (75 MHz, DMSO-d$_6$): δ 169.6, 152.7, 152.4, 145.4, 137.5, 136.3, 134.9, 134.4, 133.9, 130.9, 130.1, 129.8, 128.4, 128.1, 126.3, 126.8, 125.1, 124.2, 123.7, 122.9, 122.7, 122.2, 120.4, 113.4, 113.5, 112.4, 112.1, 108.8, 108.5, 32.5, 20.9, 13.3, 11.2. HRMS m/z: (ESI): Calculated for $C_{39}H_{31}N_3O_4S$: 638.2108 [M+H]$^+$, found 638.2137 [M+H]$^+$. IR (KBr): 2922, 1673, 1563, 1450, 1175, 577 cm$^{-1}$.

Biological Evaluation of the Compounds
Results
Cytotoxic Activity of Oxindole Derivatives In order to determine the anticancer potency, the synthesized oxindole derivatives were evaluated for anti-cancer activity various different human cancer cell lines, Leukemic Cancer (THP1), human breast cancer (MDA-MB-231 and MCF-7), human cervix carcinoma cells (HeLa), prostate cancer (DU-145) cellS by using standard Trypan blue and SRB assays. The preliminary anticancer activity for all the synthesized compounds was done at 10 μM concentration and cell inhibition was determined. Majority of the analogues were exhibited profound cytotoxicity of more than 50 percent at the preliminary anticancer evaluation.% Cell viability against different cell lines were shown in Table 1. The experiment was repeated thrice and the average values were taken.

Cell Cycle Analysis

To understand the anticancer activity mechanism of the synthesized oxindole derivatives, we analysed the cell cycle alteration phase distribution of the cells by treating THP1 cells with oxindole derivatives at 10 μM, for 24 h and analyzed by flow cytometry. Treatment of THP-1 cells with compounds 2b, 3d, 3e, 3g, 3h, 3i, 3j and 3k caused an accumulation of 98.5%, 94.3%, 96.7%, 97%, 98%, 83%, 93.5%, 98.1% cells in the G0/G1 phase respectively as compared to 68.3% in untreated cells and 99.5% in Sunitinib treated cells. All the tested compounds exhibited promising cell cycle arrest at G0/G1 phase. (Fig. x and Table .y).

VEGFR Activity:

Compounds 2b, 3d, 3e, 3g, 3h, 3i, 3j and 3k were shown inhibitory activity of VEGF tyrosin kinase activity Methods
Trypan Blue Assay The assay was carried out in a 24 well flat-bottomed microtiter tissue culture plate. THP1 cells were seeded in the plates with a density of 4×10$^4$ cells/well (counted by tryphan blue exclusion dye method). Compounds were added to obtain a concentration of 10 μM. Sunitinib was used as positive control. Plates were incubated for 48 h at 37° C. in a humidified incubator with 5% CO$_2$. At the end of the treatments, cells (THP1) were resuspended in 0.4% trypan blue and percent cell viability was counted using countess cell chamber (Life Technologies).

SRB Assay

The assay was carried out in a 24 well flat-bottomed microtiter tissue culture plate. Cells were seeded in the plates with a density of 4×10$^4$ cells/well (counted by tryphan blue exclusion dye method). After 24 hours media was replaced with fresh media and then compounds were added to obtain a concentrations of 10 μM. Sunitinib was used as positive control. Plates were incubated for 48 h at 37° C. in a humidified incubator with 5% CO$_2$. After 48 hours without removing the cell culture supernatant, 500 μl of cold 10% (wt/vol) TCA was added to each well, and the plates were incubated at 4° C. for 1 h. The plates were washed for four times with water then rinsed with water several times to remove TCA, serum, proteins and excess water was removed using paper towels and air dried. 100 μl of 0.4% (wt/vol in 1% acetic acid) SRB solution was added to each well. Plates were left at room temperature for 30 min and then the plates were quickly rinsed for four times with 1% (vol/vol) acetic acid to remove unbound dye were and then air dried until no moisture was visible. 100 μl of 10 mM Tris base solution (pH 10.5) was added to each well and shake for 5 min to solubilize the protein-bound dye. Optical density was measured at 564 nm in a micro plate reader.

Cell Cycle Analysis

The THP1 cells were treated with the active compounds at 10 concentration and incubated for about 24 h. The cells were fixed in ice cold ethanol solvent at 4° C. for about 30 minutes. The ethanol was removed and cells were treated with 1 mL of DNA staining solution (2 mg of RNase and 0.2 mg of propidium iodide (PI)) for 30 minutes. The DNA content was measured by flow cytometry (BD FACS C anto II). Results were analysed using FCS express 4 plus software.

VEGFR Activity

Phosphotyrosine (PY) Cell-Based ELISA

Briefly, cells at 60-75% confluence were placed in serum-free medium for 18 h to reduce the background of phosphorylation. Cells were then pretreated for 60 min with 2b, 3d, 3e, 3g, 3h, 3i, 3j and 3k compounds at 10 µM concentration followed by an optimized dose of purified growth factor (VEGF). The reaction was stopped, and cells were permeabilized by quickly removing the media from the cells and adding ice-cold Tris-buffered saline (TBS) containing 0.05% triton X-100, protease inhibitor cocktail, and tyrosine phosphatase inhibitor cocktail (both from Sigma Chemical). The TBS solution was then removed, and cells were fixed to the plate by heat and further incubation in 70% ethanol. Cells were further exposed to block (TBS with 1% BSA) and washed, and then a horseradish peroxidase (HRP)-conjugated phosphotyrosine antibody was added. The antibody was removed; cells were washed again and exposed to an enhanced luminol ELISA substrate, and light emission was measured using a plate reader. The known RTK-specific kinase inhibitor (Sunitinib) was used as positive control for kinase inhibition.

TABLE 2

| Sample code | Compounds | THP1-Cell Viability at 10 µM | MDA-MB-Cell 231 Viability at 10 µM | MCF-7 Cell Viability at 10 µM | HeLa Cell Viability at 10 µM | DU145 Cell Viability at 10 µM |
|---|---|---|---|---|---|---|
| INT-PRO-ACY-DP | 2a | 34.5 | 71.3 | 39.7 | 36.6 | 41.7 |
| INT-PRO-ACY-DMB | 2b | 48.5 | 42.8 | 39.8 | 40.4 | 51.2 |
| INT-FUR-DP | 3a | 53.6 | 53.8 | 51.1 | 27.6 | 21.7 |
| INT-FUR-DMB | 3b | 75.5 | 72.5 | 49.3 | 40.5 | 69.2 |
| PRO-ACY-PRY | 3c | 125.2 | 74.5 | 49.9 | 78.2 | 81.3 |
| PRO-ACY-THP | 3d | 33.3 | 35.9 | 30.7 | 71.3 | 45.5 |
| PRO-ACY-NAP | 3e | 125.2 | 85.9 | 78.2 | 152.8 | 48.2 |
| PRO-ACY-PRY-DMB | 3f | 30.2 | 37.7 | 33.1 | 39.4 | 62.1 |
| SMB-IN-OH | 3g | 104.2 | 63.8 | 91.5 | 88.3 | 94.3 |
| FUR-PRY-DP | 3h | 36.2 | 41.3 | 40.5 | 40.3 | 58.6 |
| FUR-THP-DP | 3i | 41.2 | 43.2 | 31.4 | 42.6 | 52.0 |
| FUR-NAP-DP | 3j | 83.3 | 71.3 | 37.8 | 107.2 | 45.2 |
| FUR-PRY-DMB | 3k | 80.5 | 108.6 | 43.1 | 38.9 | 62.7 |
| FUR-THP-DMB | 3l | 105.5 | 111.3 | 79.0 | 52.0 | 49.7 |
| SMB-IN-CY | 3m | 68.2 | 75.5 | 71.38 | 87.64 | 91.7 |
| SUN-STD | SUNT | 35.2 | 39.5 | 34.3 | 37.1 | 35.0 |

SUNT =

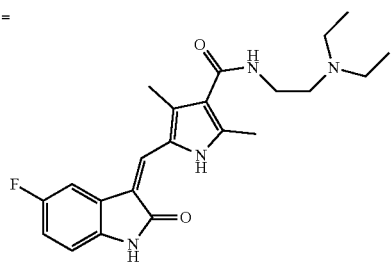

ADVANTAGES OF THE INVENTION

1. The developed process is environmental friendly since the by-product of the reaction is water.

2. The process is cost-effective and scalable as per the requirement.

We claim:

1. A compound of formula I

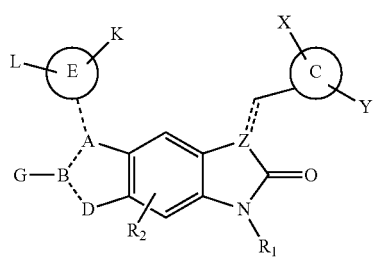

Formula I wherein,

A=C, CH, $CH_2$ or none;

B=C or CH part of open chain and/or cyclic alkyl/aryl/heteroaryl moiety;

G=alkyl, alkenyl, alkynyl, aryl, heteroaryl, heteroalkyl, alkoxy, G being optionally substituted with one or more substituents;

D=O, N, S, OH, SH, NH or None;

Z=C or $CH_2$,

Ring E=aryl, heteroaryl, cycloalkyl, Ring E being optionally substituted with one or more substituents;

Ring C=aryl, heteroaryl, cycloalkyl, Ring C being optionally substituted with one or more substituents;

L=H, alkyl, alkoxy, halogen, CN, OH, amino or $NO_2$;

K=H, alkyl, alkoxy, halogen, CN, OH, amino or $NO_2$;

X=H, alkyl, alkoxy, halogen, CN, OH, amino or $NO_2$;

Y=H, alkyl, alkoxy, halogen, CN, OH, amino or NO₂;
R1=H or alkyl; and
R2=H, alkyl, halogen, CN, NO₂, alkoxy, amino or OH.

2. The compound of formula I as claimed in claim 1, wherein the compound is selected from the group consisting of:
   i. 5-(1,3-Diphenylprop-2-yn-1-yl)-6-hydroxyindolin-2-one;
   ii. 5-(4-(Benzyloxy)-1-(2, 3-dimethoxyphenyl) but-2-ynyl)-6-hydroxyindolin-2-one;
   iii. 2-Benzyl-3-phenyl-5H-furo[3,2-f]indol-6(7H)-one;
   iv. 2-(2-(Benzyloxy) ethyl)-3-(2, 3-dimethoxyphenyl)-5H-furo [3, 2-f] indol-6(7H)-one;
   v. (Z)-3-((3,5-dimethyl-1H-pyrrol-2-yl)methylene)-5-(1, 3-diphenylprop-2-yn-1-yl)-6-hydroxyindolin-2-one;
   vi. (Z)-5-(1,3-diphenylprop-2-yn-1-yl)-6-hydroxy-3-((3-methylthiophen-2-yl)methylene)indolin-2-one;
   vii. (Z)-3-((4-(dimethylamino)naphthalen-1-yl)methylene)-5-(1,3-diphenylprop-2-yn-1-yl)-6-hydroxyindolin-2-one;
   viii. (Z)-5-(3-(benzyloxy)-1-(2,3-dimethoxyphenyl)prop-2-yn-1-yl)-3-((3,5-dimethyl-1H-pyrrol-2-yl)methylene)-6-hydroxyindolin-2-one;
   ix. (Z)-3-((3,5-dimethyl-1H-pyrrol-2-yl)methylene)-6-hydroxy-5-(3-phenyl-1-(1-tosyl-1H-indol-3-yl)prop-2-yn-1-yl)indolin-2-one;
   x. (Z)-2-benzyl-5-((3,5-dimethyl-1H-pyrrol-2-yl)methylene)-3-phenyl-5H-furo[3,2-f]indol-6(7H)-one;
   xi. (Z)-2-benzyl-5-((3-methylthiophen-2-yl)methylene)-3-phenyl-5H-furo[3,2-f]indol-6(7H)-one;
   xii. (Z)-2-benzyl-5-((4-(dimethylamino)naphthalen-1-yl)methylene)-3-phenyl-5H-furo[3,2-f]indol-6(7H)-one;
   xiii. (Z)-2-((benzyloxy)methyl)-3-(2,3-dimethoxyphenyl)-5-((3,5-dimethyl-1H-pyrrol-2-yl)methylene)-5H-furo[3,2-f]indol-6(7H)-one;
   xiv. (Z)-2-((benzyloxy)methyl)-3-(2,3-dimethoxyphenyl)-5-((3-methylthiophen-2-yl)methylene)-5H-furo[3, 2-f]indol-6(7H)-one; and
   xv. (Z)-2-benzyl-5-((3,5-dimethyl-1H-pyrrol-2-yl)methylene)-3-(1-tosyl-1H-indol-3-yl)-5H-furo[3,2-f]indol-6(7H)-one.

3. A process for the preparation of compound of formula I as claimed in claim 1, the process comprising the steps of:
   a) alkylating an oxindole compound of formula 1 with a compound of formula (a) at a temperature in the range of 65 to 75° C. for a period of time in the range of 3 to 5 h followed by purifying to obtain a compound of formula 2; and

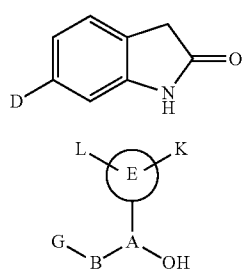

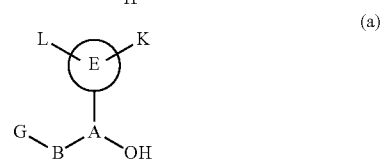

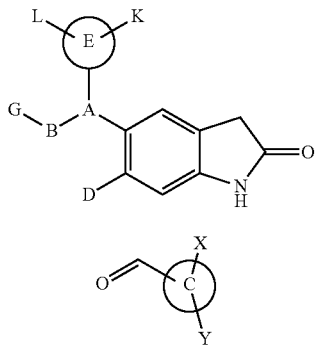

b) cyclizating the compound of formula 2 as obtained in step a) using a base at a temperature in the range of 70 to 80° C. for a period of time in the range of 3-5 h followed by purifying to obtain a compound of formula I; or c) condensating the compound of formula 2 as obtained in step a) with an aldehyde of formula (c) at an active methylene of the oxindole compound of formula 1 at a temperature in the range of 70 to 80° C. for a period of time in the range of 3-5 h, and purifying to obtain a compound of formula I; or d) cyclizating the compound of formula 2 as obtained in step a) using base at a temperature in the range of 70 to 80° C. for a period in the range of 3-5 h followed by condensating with an aldehyde of formula (c) at an active methylene of the oxindole compound of formula 1 at a temperature in the range of 70 to 80° C. for a period of time in the range of 3-5 h, and purifying to obtain a compound of formula I.

4. The process as claimed in step a) of claim 3, wherein alkylation is performed using an acid catalyst, nitromethane and THF (tetrahydrofuran).

5. The process as claimed in step b) of claim 3, wherein the base used is selected from the group consisting of K₂CO₃, NaOH, KOH, Na₂CO₃ or NaHCO₃.

6. The process as claimed in step b) of claim 3, wherein condensation reaction with the aldehyde is carried out in an alcoholic solvent and an organic base.

7. The process as claimed in claim 6, wherein the alcoholic solvent used is selected from the group consisting of methanol, ethanol, propanol or butanol.

8. The process as claimed in claim 6, wherein the organic base used is selected from the group consisting of piperidine, pyrrolidine or trimethylamine.

9. The compound of formula I as claimed in claim 1 for use as anti-cancer agents.

10. The compound of formula I as claimed in claim 1, wherein percentage of cell viability against different cancer cell lines ranging between 20 to 160% at 10 μM.

* * * * *